Figure 2A:
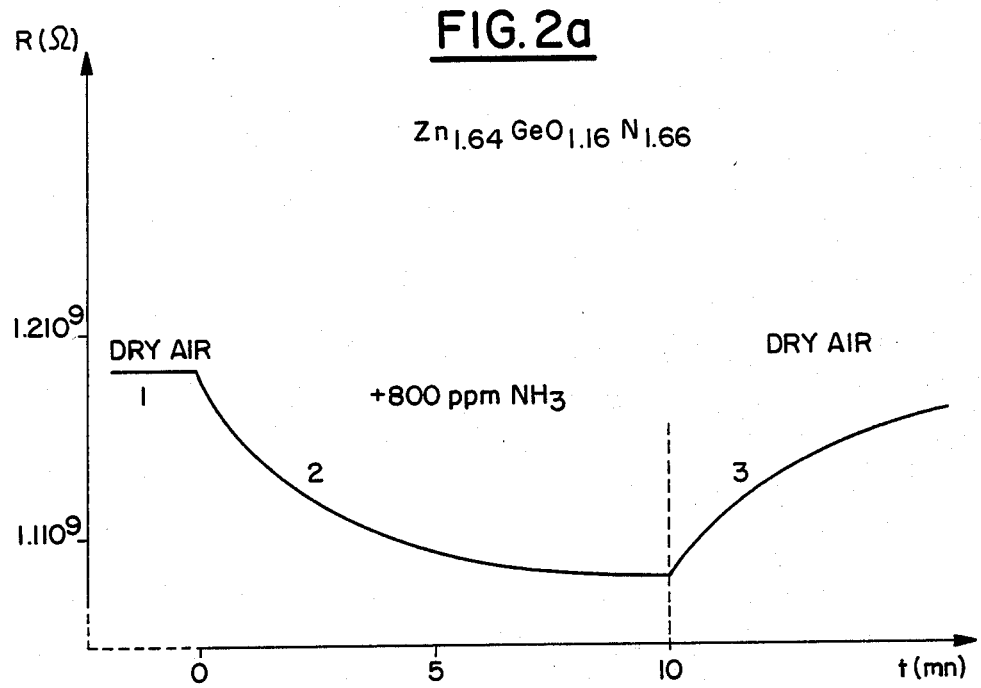

United States Patent [19]

Merdrignac et al.

[11] Patent Number: 4,983,360
[45] Date of Patent: Jan. 8, 1991

[54] GALLIUM NITRIDE AND OXYNITRIDES USED AS SELECTIVE DETECTORS OF REDUCING GASES, PROCESS OF MAKING AND DEVICE CONTAINING THEM

[75] Inventors: Odile Merdrignac, Lamballe; Jean Guyader; Patrick Verdier, both of Acigne; Yves Colin; Yves Laurent, both of Cesson-Sevigne, all of France

[73] Assignee: Centre National De La Recherche Scientifique, Paris, France

[21] Appl. No.: 430,515

[22] Filed: Nov. 1, 1989

[30] Foreign Application Priority Data

Nov. 2, 1988 [FR] France ............... 8814270

[51] Int. Cl.$^5$ ............ H01C 7/00; G01N 27/00; G01N 27/04; G01N 33/00
[52] U.S. Cl. ............................ 422/90; 338/34; 422/98; 436/111; 436/114
[58] Field of Search ............. 422/90, 98; 436/114, 436/111, 151, 181; 204/415, 416; 338/34

[56] References Cited

U.S. PATENT DOCUMENTS

| | | | |
|---|---|---|---|
| 3,732,519 | 5/1973 | Taguchi | 338/34 |
| 3,865,550 | 2/1975 | Bott et al. | 436/134 |
| 4,045,178 | 8/1977 | Okinaka et al. | 422/98 |
| 4,045,764 | 8/1977 | Ichinose et al. | 338/34 |
| 4,197,089 | 4/1980 | Willis et al. | 436/121 |
| 4,259,292 | 3/1981 | Ichinose et al. | 338/34 |
| 4,509,034 | 4/1985 | Sakai | 338/34 |
| 4,695,432 | 9/1987 | Colin et al. | 436/111 |
| 4,885,929 | 12/1989 | Kasahara et al. | 422/98 |

Primary Examiner—Robert J. Warden
Assistant Examiner—Thalia P. Vassilatos
Attorney, Agent, or Firm—Blakely, Sokoloff, Taylor & Zafman

[57] ABSTRACT

The present invention relates, a compound for use with selective detectors of the semiconductor resistance type which detect for nitrogenous reducing gases in the atmosphere, especially ammonia and gases containing NH and/or $NH_2$ groups, said compound comprising the gallium nitride and, oxynitrides of tetrahedral structure according to the general formula:

$$Ga_{1-\frac{x}{3}}\square_{\frac{x}{3}}N_{1-x}O_x$$

in which:
$\square$ represents a hole, and $0 \leq x \leq 0.3$.

9 Claims, 2 Drawing Sheets

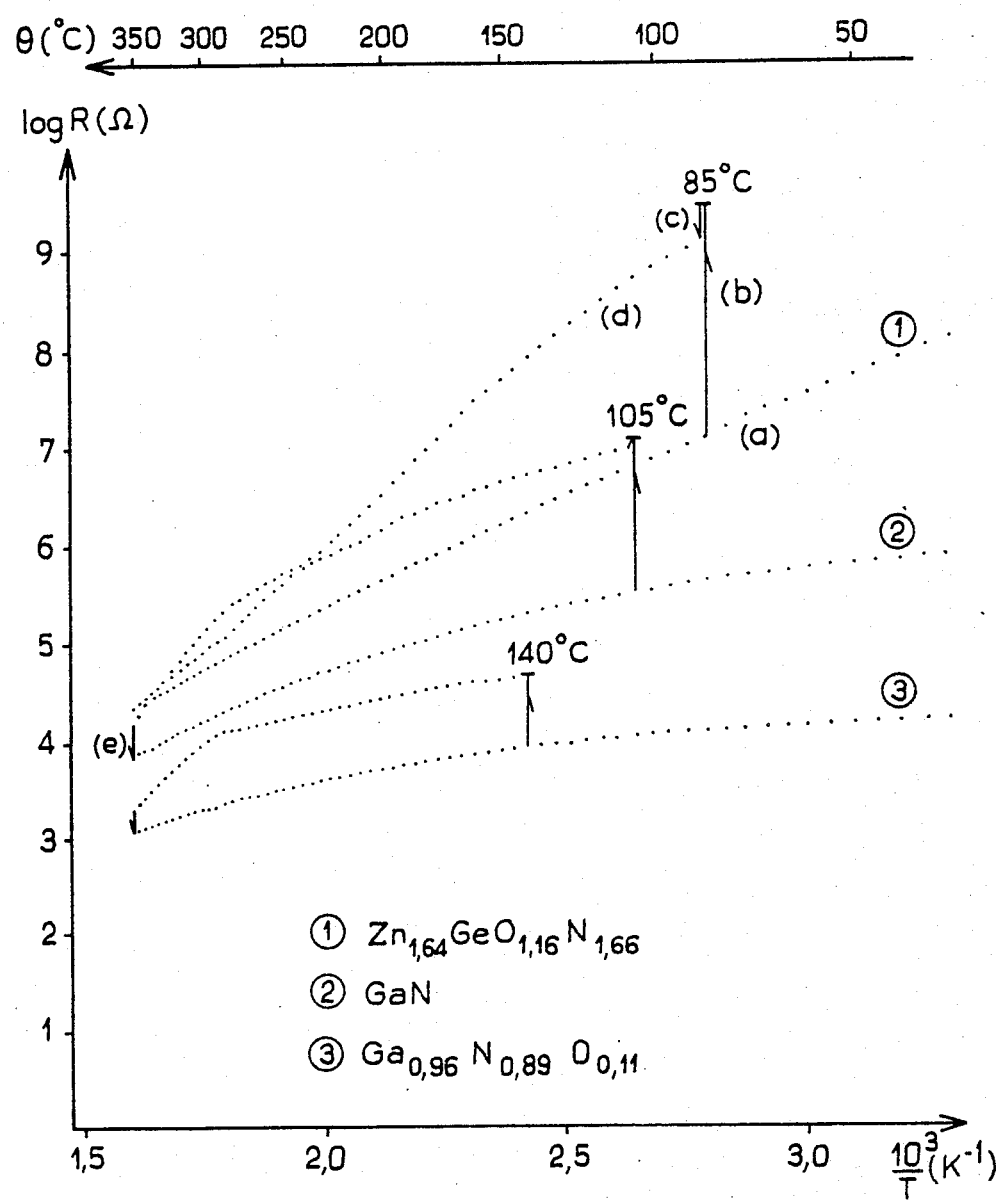
FIG_1

GALLIUM NITRIDE AND OXYNITRIDES USED AS SELECTIVE DETECTORS OF REDUCING GASES, PROCESS OF MAKING AND DEVICE CONTAINING THEM

The present invention relates to gallium nitride and oxynitrides which can be used as selective detectors of nitrogenous reducing gases in the atmosphere, especially of ammonia and of gases containing NH and/or NH$_2$ groups, their process of preparation, as well as selective detection devices containing said nitride and oxynitrides.

In the prior art, the majority of gas sensors utilizing as detection parameter the electrical resistance of a semiconductor layer use oxides which are doped to a greater or lesser extent, such as SnO$_2$ or ZnO, which are relatively sensitive to various reducing gases. However, none of them, irrespective of the physicochemical phenomenon on which its operation is based, is particularly selective for the nitrogenous reducing gases and especially for ammonia, with a desirable reliability. All these sensors exhibit average qualities of sensitivity, selectivity and reliability; furthermore, they demand a significant level of maintenance. It is absolutely impossible to use them effectively as selective sensors, for example, of ammonia.

It was then recommended to use, by way of such selective sensors, double oxynitrides and nitrides, especially compounds according to the general formula Zn$_t$Ge$_u$O$_v$N$_w$ (see FR-A-2,579,754).

However, these double oxynitrides and nitrides exhibit certain disadvantages which, in practice, make their use difficult as selective sensors of nitrogenous reducing gases.

First of all, these earlier compounds exhibit very high resistances, in the order of 10$^9$Ω; this necessitates the use of resistance measuring devices the design of which is relatively sophisticated and the space requirement of which is relatively large.

Moreover, these compounds exhibit large variations of their electrical resistance as a function of temperature. This necessitates the use of very accurate devices for regulating the temperature of use, in order to obtain reliable measurements.

The object of the present invention was specifically to overcome these disadvantages and, consequently, to find other semiconductor compounds which are more stable as a function of temperature, especially in the presence of ammonia or of moisture, while remaining entirely capable of adsorbing oxygen in such a manner as to promote the detection of nitrogenous reducing gases and more specifically of ammonia.

According to the present invention, use will be made, by way of selective detectors of nitrogenous reducing gases in the atmosphere, of especially ammonia and gases containing NH and/or NH$_2$ groups, of gallium nitride and oxynitrides having a tetrahedral structure according to the general formula:

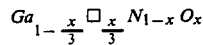

in which:
☐ represents a hole, and 0 ≦ X ≦ 0.3.

Given that these gallium oxynitrides and nitride are produced under ammonia and are physically very stable at the usual temperatures, they exhibit the decisive advantage of not reacting directly with ammonia at these temperatures. On the other hand, the oxygen of the air which they adsorb by a phenomenon of strong chemisorption reacts reversibly with the nitrogenous reducing gases such as ammonia within a range of temperatures which is dependent, in particular, upon the conditions of preparation influencing the stoichiometry of the compounds according to the invention.

The gallium nitride and oxynitrides according to the invention may advantageously be prepared by the reaction of a gallium oxide with ammonia at a temperature exceeding approximately 550° C.

Gallium nitride GaN is advantageously obtained by reaction of gallium oxide Ga$_2$O$_3$ with ammonia at a temperature approximately within the range between 550° C. and 900° C.

Gallium nitride is easily separated from the reaction medium.

It should be noted at this point that, by operating at a temperature in the order of 850 to 900° C, in the presence of a gas throughput of approximately 10 liters/hour of ammonia, very rapid reaction kinetics are observed.

To prepare the gallium oxynitrides, a gallate is reacted with ammonia at a temperature substantially within the range between 550 and 650° C., and the oxynitride thus obtained is separated from the reaction medium. Such a separation is carried out under excellent conditions by fractional dissolution in a nitric acid medium.

In practice, various starting gallates have been used satisfactorily. By way of example, mention will be made principally of double oxides selected from MgGa$_2$O$_4$, MnGa$_2$O$_4$, ZnGa$_2$O$_4$, FeGa$_2$O$_4$, Fe$_{0.2}$Ga$_{1.8}$O$_3$, Ga$_4$GeO$_8$, NiGa$_2$O$_4$, CuGaO$_2$, CuGa$_2$O$_4$.

It will briefly be stated that the aforementioned double oxides are prepared in a conventional manner, for example under dry conditions from the corresponding simple oxides.

According to an additional feature of the process forming the subject of the present invention, the oxynitride separated from the reaction medium is subjected to a subsequent treatment of stabilization by heating to a temperature in the order of 200 to 300° C. under a gas current of ammonia.

Advantageously, such a stabilization treatment will be conducted immediately after production and separation of the oxynitride. This treatment ensures a complete reversibility of the sensor and, accordingly, a stabilization of its responses. Following this treatment, a slight increase in the electrical resistance of the stabilized gallium oxynitrides is observed. This increase in the resistance may be reduced greatly if the heat treatment is carried out immediately after the oxynitride has been obtained.

In practice, an excellent stabilization of the gallium oxynitrides according to the invention is obtained by utilizing a heat treatment, between 200 and 300° C., with circulation of an air flow having an NH$_3$ concentration in the order of 1,500 ppm.

In general, a heat treatment duration of at least approximately 15 minutes proves to be sufficient However, the precise duration of this heat treatment may vary to some extent as a function of the temperature and of the ammonia concentration of the gas flow used for the treatment.

These proposed oxynitrides and nitride possess a concentration of electrons of valency greater than or equal to 4 and exhibit a tetrahedral structure derived from that of wurtzite with occupation by gallium of one half of the tetrahedral sites of the anionic lattice. Such nitride and oxynitrides are present in the form of powders, which it is possible to pelletize under pressure or alternatively to deposit in the form of a thick layer.

Accordingly, these oxynitrides and nitride may advantageously be used for the production of devices for the selective detection, in the atmosphere, of nitrogenous reducing gases and in particular of ammonia as well as other gases containing the NH and/or $NH_2$ groups.

According to the present invention, such a detection device comprises a semiconductor layer based on such a nitride or oxynitride placed on a support equipped with a heating means which is capable, for example, of reaching a temperature of approximately 250° C., as well as a means for measuring the variation of the resistance of said layer in response to the chemisorption of the nitrogenous reducing gases on said layer, the measuring means supplying a signal representative of the variation of the concentration of said gases in the vicinity of this layer. Depending upon the particular applications under consideration, the signal concerned may be an audible or luminous signal, or alternatively the display of a content of nitrogenous reducing gases on a graduated scale, for example directly in ppm of ammonia Such devices for selective detection in the atmosphere of nitrogenous reducing gases are used, for example, in refrigerating installations equipped with alarm thresholds. It should, in fact, be recalled that at the present time a large majority of refrigerant fluids used consist of ammonia.

Such detectors are also used in the dairy industry, the nitric acid and animal feedstuffs industry, canneries, tanneries, stock farms and abattoirs, where animal waste is burnt.

Such detection devices are also used in the field of the enrichment of soils in nitrogen by direct injection of ammonia. The subject of the present invention further permits the assurance of a monitoring of silos in which cattle feed is supplemented with nitrogenous material, for example by injection of anhydrous ammonia at the time when the maize is fed into the silo filler. It will likewise be stated that in the field of agricultural feeds, ammonia frequently accompanies other atmospheric pollutants. Accordingly, the detection of the ammonia permits the prevention not only of the appearance of this gas at unacceptable or dangerous levels, but also of that of accompanying gases.

Various experiments have been carried out in order to verify the conditions of chemisorption and of desorption of the oxygen as well as the range of optimal temperatures for reversible reaction of ammonia with the adsorbed oxygen.

The various characteristic properties of the compounds according to the present invention are, on a global basis, of the same order as those of the double oxides of the prior art illustrated by FR-A-2,579,754.

The curves of the accompanying figures do, however, demonstrate clearly the decisive improvements which are exhibited by the compounds according to the invention in comparison with a double oxide of zinc and of germanium according to the prior art.

Figure 2B:
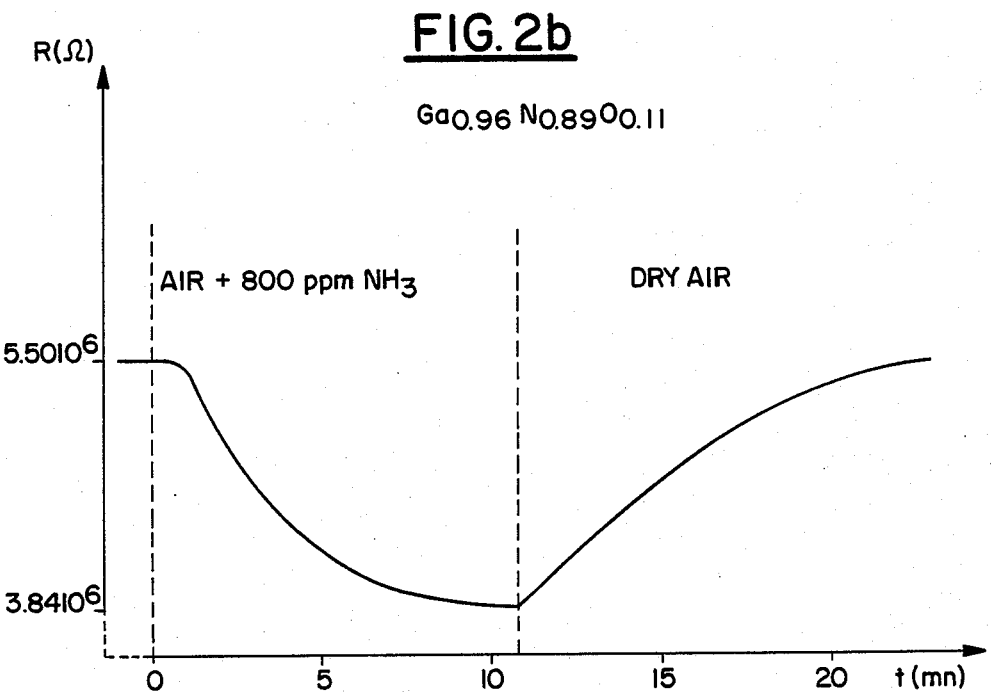

In the accompanying figures, FIG. 1 represents three comparative curves illustrating the modifications of the electrical conductivity of three samples of nitride and of oxynitrides, under the effect of the chemisorption of oxygen and of the desorption programmed as a function of the thermodynamic temperature. In this figure, a) represents the reference curve Log Ro (1/T),
b) represents isothermal chemisorption,
c) represents isothermal desorption,
d) represents the curve of desorption temperature-programmed at 3 K/min,
e) represents isothermal desorption at 350° C. FIG. 2 represents the variations of resistance of oxynitrides due to the action of ammonia; the upper diagram corresponds to a sample of double oxide of zinc and germanium according to the aforementioned prior art, and the lower diagram relates to a sample of gallium oxynitride forming the subject of the present application.

The comparative analysis of the various diagrams of the accompanying FIGS. 1 and 2 shows clearly the improvements consequent upon the use of gallium nitride or oxynitrides according to the invention.

There is found, in particular, a very marked reduction, approximately three orders of magnitude, in the resistance of the compounds forming the subject of the present application.

FIG. 1 also reveals a very great reduction of the gradient of the curves of variation of the resistance as a function of the temperature.

Accordingly, these experiments demonstrate clearly the benefit offered by the compounds forming the subject of the present application. They especially permit a far easier construction of selective sensors of gases. In fact, on the one hand, the lower resistances are easier to measure and, on the other hand, the very small variations of electrical resistance as a function of the temperature do not require a very precise regulation of the temperature of use of these sensors.

Mention will be made, hereinbelow, by way of illustration, of a few particular examples of preparation of compounds according to the invention.

At a temperature of 580° C., ammonia is reacted with nickel gallate $NiGa_2O_4$ for a period of several days. This reaction leads to a mixture of an alloy $Ni_3Ga$ and a gallium oxynitride, of black color. The separation is carried out by fractional dissolving in a N/10 nitric acid medium. The residue of yellow color, which is taken up by absolute alcohol, is dried at 20° C. under vacuum. The analysis of the product obtained, which is symbolized by X, gives the following results:

Ga : 82.6%
N : 15.5%
Ga/N : 1.07%

In view of the accuracy of the assays, an oxygen level within the range between 1 and 2.5% is deduced therefrom by difference.

Depending upon the nature of the starting gallates and upon the experimental conditions, the products mentioned in Table I hereinbelow are obtained.

TABLE 1

| DOUBLE OXIDE | REACTION TEMPERATURE | REACTION PRODUCT |
|---|---|---|
| $MgGa_2O_4$ | 900 | GaN + MgO |
| $MnGa_2O_4$ | 800 | GaN + MnO |
|  | 950 | GaN + $Mn_6N_5$ |
| $ZnGa_2O_4$ | 600 | X + Zn |

TABLE 1-continued

| DOUBLE OXIDE | REACTION TEMPERATURE | REACTION PRODUCT |
|---|---|---|
| FeGaO$_3$ | 800 | GaN + Fe$_3$N |
| Fe$_{0.2}$Ga$_{1.6}$O$_3$ | 750 | X + Ge$_3$N |
| Ga$_4$GeO$_8$ | 750 | GaN + Ge$_3$N$_4$ |
| NiGa$_2$O$_4$ | 550 < t < 650 | X + Ni$_3$Ga |
| CuGaO$_2$ | 500–550 | X + Cu |
| CuGa$_2$O$_4$ | 500–550 | X + Cu |

The nitrogen content shows a deficit as compared with that of the nitride GaN, the calculated contents of which are: Ga%: 83.27; N%: 16.73. Its value is in agreement with that which is deduced from the increase in mass in the course of the reaction of X with oxygen.

The X powder diagram is comparable with that of the nitride GaN; this shows all the reflections specific to the latter at the same angles of diffraction, but the relative intensities are very different. Furthermore, three supplementary reflections of low intensity are observed.

The entire diagram is indexed with a hexagonal grid of parameters: a=a$_0$=3.18$_6$Å; c=3c$_0$=3×5.17$_8$Å=15.5$_3$Å. a$_0$ and c$_0$ are the parameters of GaN; thus, all the reflections remain compatible with the spatial grid P6$_3$mc of wurtzite.

The comparison of the powder diagrams of the phase X and GaN shows that all the reflections which are specific or of increased intensity in X are compatible with a cubic lattice of the sphaleric type (G.S.=F43m) of parameter : a′=a$_0$√2=5.50$_5$Å (see Table II hereinbelow).

The phase X is not a mixture containing gallium nitride, since it completely dissolves in concentrated and hot acids in which GaN remains inert. Accordingly, it is a polytype in which the two types of hexagonal close packed and face centered cubic structure coexist.

In order to maintain a concentration of electrons of valency equal to 4, this being the condition for the existence of a tetrahedral structure, it is necessary to formulate X as follows:

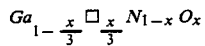

In this particular example, the chemical analysis gives x=0.09$_5$.

TABLE II

| | Phase X | | | | GaN | |
|---|---|---|---|---|---|---|
| | hkl a = 3.18$_6$Å | | hkl a′ = 4.50$_5$Å | | hkl a$_0$ = 3.18$_6$Å | |
| d(Å) | c = 15.5$_3$Å | I/I$_0$ | | I/I$_0$ | c$_0$ = 5.17$_8$Å | |
| 2.76 | 1 0 0 | 43 | — | 48 | 1 0 0 | |
| 2.59 | 0 0 6 | 100 | 1 1 1 | 50 | 0 0 2 | |
| 2.43 | 1 0 3 | 80 | — | 100 | 1 0 1 | |
| 2.25 | 1 0 4 | 10 | 2 0 0 | — | — | |
| 1.884 | 1 0 6 | 8 | — | 16 | 1 0 2 | |
| 1.591 | 1 1 0 | 45 | 2 2 0 | 29 | 1 1 0 | |
| 1.461 | 1 0 9 | 14 | — | 28 | 1 0 3 | |
| 1.382 | 2 0 0 | 4 | — | 4 | 2 0 0 | |
| 1.357 | 1 1 6 | 36 | 3 1 1 | 24 | 1 1 2 | |
| 1.333 | 2 0 3 | 10 | — | 13 | 2 0 1 | |
| 1.295 | 0 0 12 | 6 | 2 2 2 | 3 | 0 0 4 | |
| . | | | | | | |
| . | | | | | | |
| 1.125 | 2 0 8 | <1 | 4 0 0 | — | — | |
| . | | | | | | |
| . | | | | | | |
| 1.034 | 2 1 2 | 2 | 3 3 1 | — | — | |

Finally, it will be stated that by varying the reaction duration it is possible to modify the relative proportions of the various elements making up the gallium oxynitrides according to the invention. Thus, starting from the same nickel gallate, the reaction with ammonia at 580° C. leads to the following oxynitrides, as a function of the reaction time:

| 6 DAYS | Ga 0.951 | N 0.854 | O 0.146 |
|---|---|---|---|
| 8 DAYS | Ga 0.963 | N 0.888 | O 0.112 |
| 12 DAYS | Ga 0.931 | N 0.792 | O 0.208 |

We claim:

1. A compound for use with selective detectors of the semiconductor resistance type which selectively detect for nitrogenous reducing gases in the atmosphere, especially ammonia and gases containing NH and/or NH$_2$ groups, said compound comprising gallium nitride and oxynitrides of tetrahedral structure according to the general formula:

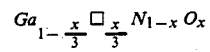

in which:
□ represents a hole, and 0≦ X ≦0.3.

2. A process for the preparation of gallium nitride and oxynitrides, as defined in claim 1, wherein a gallium oxide is reacted with ammonia at a temperature exceeding approximately 550° C.

3. The process as claimed in claim 2, wherein Ga$_2$O$_3$ is reacted with ammonia at a temperature approximately within the range between 550° C. and 900° C., and wherein the nitride obtained is separated from the reaction medium.

4. The process as claimed in claim 2, wherein a gallate is reacted with ammonia at a temperature substantially within the range between 550° C. and 650° C., and wherein the oxynitride obtained is separated from the reaction medium.

5. The process as claimed in claim 4, wherein the gallate is a double oxide selected from among MgGa$_2$O$_4$, MnGa$_2$O$_4$, ZnGa$_2$O$_4$, FeGaO$_3$, Fe$_{0.2}$Ga$_{1.8}$O$_3$, Ga$_4$GeO$_8$, NiGa$_2$O$_4$, CuGaO$_2$, CuGa$_2$O$_4$.

6. The process as claimed in one of claims 4 and 5, wherein the oxynitride obtained is separated from the reaction medium by fractional dissolving in a nitric acid medium.

7. The process as claimed in one of claims 4 and 5, wherein the oxynitride is subjected to a subsequent treatment of stabilization by heating to a temperature in the order of 200° C. to 300° C., under a gas current of ammonia.

8. The process as claimed in claim 7, wherein the stabilization treatment is effected immediately after the production and the separation of the oxynitride from the reaction medium.

9. A device for the selective detection, in the atmosphere, of nitrogenous reducing gases, especially of ammonia and of gases containing NH and/or NH$_2$ groups, which comprises a semiconductor layer based on a nitride or oxynitride as claimed in claim 1, placed on a support equipped with a heating means, and a means for the measurement of the variation of the resistance of said layer in response to the chemisorption of the nitrogenous reducing gases on said layer, the measuring means supplying a signal representative of the variation of the concentration of said gases in the vicinity of said layer.

* * * * *

UNITED STATES PATENT AND TRADEMARK OFFICE
CERTIFICATE OF CORRECTION

| | | |
|---|---|---|
| PATENT NO. | : | 4,983,360 |
| DATED | : | January 8, 1991 |
| INVENTOR(S) | : | Merdrignac et al. |

It is certified that error appears in the above-identified patent and that said Letters Patent is hereby corrected as shown below:

ON THE THE TITLE PAGE:

[73] Assignee  delete "Centre National De la Recherche Scientifique"

insert --Centre National de la Recherche Scientifique (CNRS) Paris, France; Universite de Rennes I, Rennes, France--

| | | |
|---|---|---|
| col. 02, line 62 | after "sufficient" | insert --.-- |
| col. 05, line 37 | delete ".to" | insert --to-- |

Signed and Sealed this

Twenty-third Day of November, 1993

*Attest:*

BRUCE LEHMAN

*Attesting Officer*     *Commissioner of Patents and Trademarks*